(12) United States Patent
Huang et al.

(10) Patent No.: US 11,786,154 B2
(45) Date of Patent: Oct. 17, 2023

(54) BIOSENSING DEVICE AND ACTIVATION METHOD THEREOF

(71) Applicant: BIONIME CORPORATION, Taichung (TW)

(72) Inventors: Chun-Mu Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 0 days.

(21) Appl. No.: 17/850,193

(22) Filed: Jun. 27, 2022

(65) Prior Publication Data

US 2022/0322979 A1 Oct. 13, 2022

Related U.S. Application Data

(63) Continuation of application No. 16/884,422, filed on May 27, 2020, now Pat. No. 11,517,229.

(30) Foreign Application Priority Data

May 29, 2019 (TW) .................................. 108118609

(51) Int. Cl.
*A61B 5/1486* (2006.01)
*A61B 5/00* (2006.01)
*A61B 5/145* (2006.01)

(52) U.S. Cl.
CPC ........ *A61B 5/14865* (2013.01); *A61B 5/6849* (2013.01); *A61B 5/14532* (2013.01); *A61B 2560/0214* (2013.01); *A61B 2560/0443* (2013.01); *A61B 2562/227* (2013.01)

(58) Field of Classification Search
CPC ....... A61B 5/1486; A61B 5/00; A61B 5/6849; A61B 5/6848; A61B 5/14865; A61B 5/1451; A61B 5/14532; A61B 2562/227; A61B 2560/063; A61B 2560/045; A61B 5/688; A61B 2560/0214; A61B 2560/0443
See application file for complete search history.

(56) References Cited

U.S. PATENT DOCUMENTS

| 6,175,752 B1 | 1/2001 | Say et al. |
| 2007/0227907 A1 | 10/2007 | Shah et al. |

(Continued)

OTHER PUBLICATIONS

Extended European Search Report for European Application No. 20176776.1, dated Oct. 8, 2020.

*Primary Examiner* — Eric J Messersmith
(74) *Attorney, Agent, or Firm* — Birch, Stewart, Kolasch & Birch, LLP

(57) ABSTRACT

A biosensing device includes a sensor module and an electric signal transducer. The sensor module includes a biosensor adapted for measuring a biosignal of a host, and a fixed seat including a conducting member that is electrically connected to the biosensor. The electric signal transducer is for receiving and sending the biosignal measured by the biosensor, is coupled to the sensor module, and includes an electric signal unit electrically connected to the conducting member, and a battery connected to the electric signal unit. The electric signal unit has two electrical contacts that cooperatively define a switch. The battery provides power supply to the biosensor when the electric signal transducer is coupled to the sensor module.

4 Claims, 23 Drawing Sheets

(56) References Cited

U.S. PATENT DOCUMENTS

| | | | |
|---|---|---|---|
| 2011/0213225 A1* | 9/2011 | Bernstein | G16H 40/67 |
| | | | 600/309 |
| 2016/0058470 A1 | 3/2016 | Peterson et al. | |
| 2017/0290533 A1* | 10/2017 | Antonio | A61B 5/14532 |
| 2018/0271414 A1 | 9/2018 | Deck et al. | |
| 2018/0317820 A1 | 11/2018 | Pace et al. | |
| 2018/0368774 A1* | 12/2018 | Gray | A61B 5/0004 |
| 2019/0142315 A1 | 5/2019 | Love et al. | |

* cited by examiner

BIOSENSING DEVICE AND ACTIVATION METHOD THEREOF

CROSS-REFERENCE TO RELATED APPLICATION

This is a continuation application of U.S. patent application Ser. No. 16/884,422, filed on May 27, 2020, which claims priority of Taiwanese Patent Application No. 108118609, filed on May 29, 2019.

FIELD

The disclosure relates to a sensor, and more particularly to a biosensing device.

BACKGROUND

Referring to FIGS. 1 to 3, a conventional sensing device 1 disclosed in U.S. Pat. No. 7,899,511 includes a base 12, an adhesive pad 11 that is adapted for adhering the base 12 onto a host's skin (not shown), a mounting seat 13 that is mounted in the base 12, a biosensor 14 that is installed to the mounting seat 13, and an electronics unit 15 that is mounted to the base 12 and that is connected to the biosensor 14.

In installation of the sensing device 1, after the base 12 is adhered onto the host's skin via the adhesive pad 11, the biosensor 14, which has been installed to the mounting seat 13 beforehand, is inserted to the base 12 (see FIG. 2) via an insertion tool (not shown). Then, the mounting seat 13 is rotated to bend an output section 141 of the biosensor 14 (see FIG. 3), so that the biosensor 14 is electrically connected to the electronics unit 15. In another installation way of the sensing device 1, the biosensor 14 is bent to a predetermined angle before being inserted to the base 12.

Since the biosensor 14 must be bent to establish electric connection to the electronics unit 15 so that the electronics unit 15 can read biosignals, a bent section of the biosensor 14 tends to be subjected to a relatively large internal stress, which can damage the biosensor 14 itself. As such, the biosensor 14 is inherently more prone to breakage whenever it is inserted or retrieved. In addition, internal circuit of the electronics unit 15 is in a closed-circuit state, such that it consumes electric power whether or not it is electrically connected to the biosensor 14.

SUMMARY

Therefore, an object of the disclosure is to provide a biosensing device and an activation method thereof that can alleviate at least one of the drawbacks of the prior art.

According to one aspect the disclosure, the biosensing device includes a sensor module and an electric signal transducer. The sensor module includes a biosensor adapted for measuring a biosignal of a host, and a fixed seat for the biosensor to be mounted thereto. The fixed seat includes an electric connection unit that includes at least one conducting member electrically connected to the biosensor. The conducting member includes a plurality of conductive layers and a plurality of insulating layers that are disposed in an alternating arrangement along a direction a first axis.

The electric signal transducer is for receiving and sending the biosignal measured by the biosensor, is coupled to the sensor module along a direction of second axis, which is not parallel to the first axis, and includes an electric signal unit that is electrically connected to the at least one conducting member, and a battery that is connected to the electric signal unit. The electric signal unit has two electrical contacts that cooperatively define a switch which is in an open circuit state by default. The battery provides power supply to the biosensor when the electric signal transducer is coupled to the sensor module.

According to another aspect of the disclosure, a biosensing device activation method includes steps of:

a) mounting a biosensor and a conducting member to a fixed seat to form a sensor module, the conducting member including a plurality of conductive layers and a plurality of insulating layers that are disposed in an alternating arrangement along a direction of a first axis;

b) coupling the sensor module to an insertion tool, and coupling the sensor module to a guiding needle;

c) coupling an electric signal transducer to an insertion tool along a direction of a second axis not parallel to the first axis, two electrical contacts of the electric signal transducer being in an open circuit state;

d) placing the insertion tool on a skin surface of a host, and applying pressure such that the electric signal transducer is attached to the skin surface;

e) coupling the sensor module to a base of the electric signal transducer while simultaneously inserting a sensing section of the biosensor into the host;

f) pushing the sensor module to a starting position via the insertion tool, thereby prompting electric contact between the conducting member and the electrical contacts of the electric signal transducer; and g) initiating the battery of the electric signal transducer to supply power to the sensor module, thereby allowing the biosensing device to perform testing.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
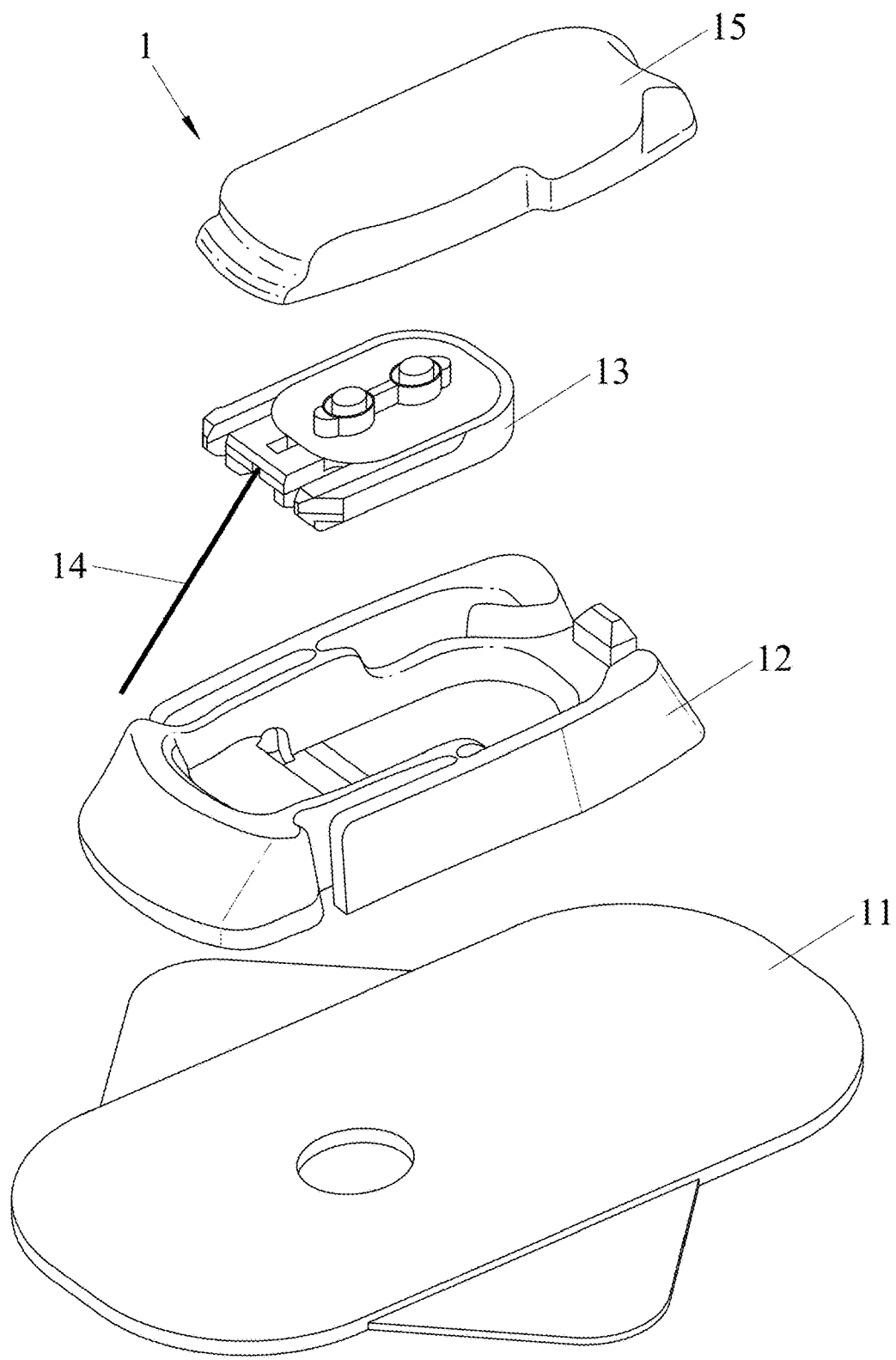
FIG. 1 is an exploded perspective view of a conventional sensing device.
Figure 2:
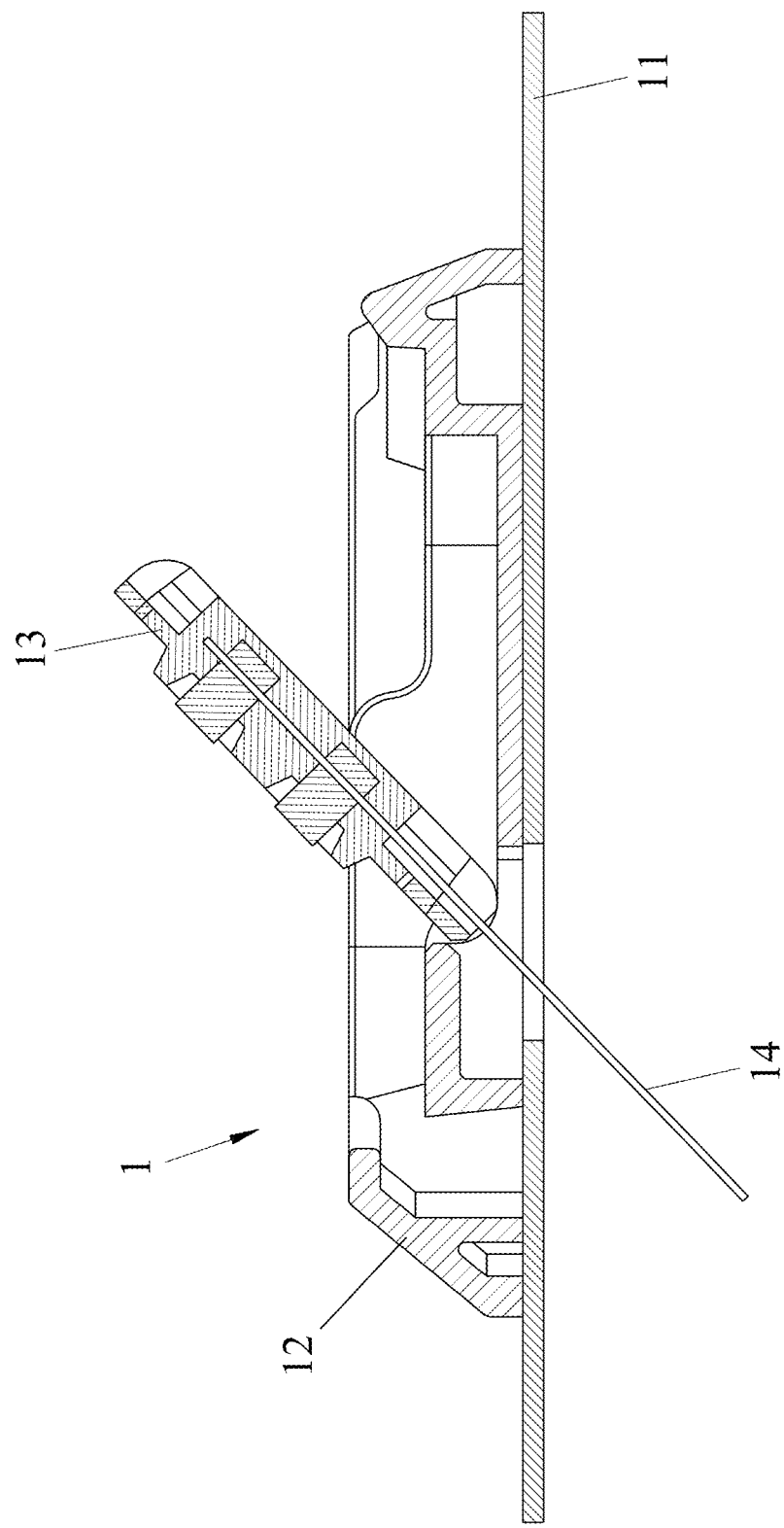
FIG. 2 is a side sectional view of the conventional sensing device, illustrating a mounting seat being inserted to a base.
Figure 3:
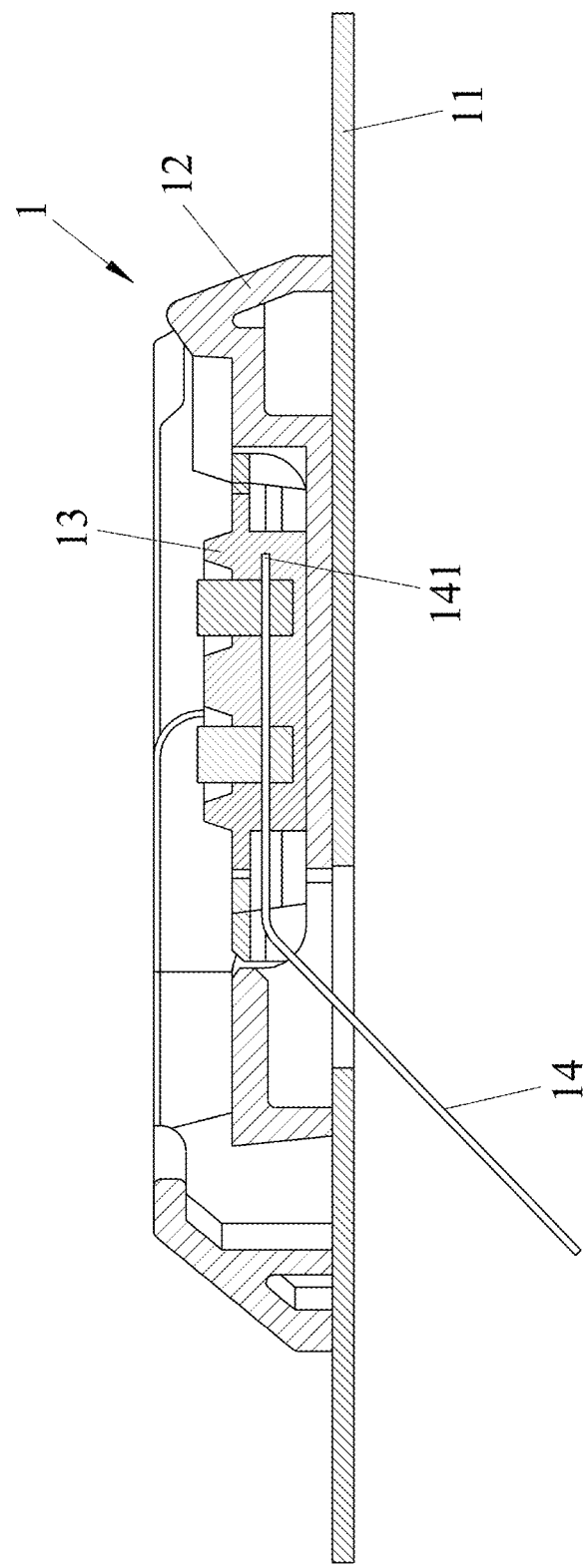
FIG. 3 is a view similar to FIG. 2, illustrating the mounting seat being properly mounted to the base and a biosensor being bent to be connected to the base

Before the disclosure is described in greater detail, it should be noted that where considered appropriate, reference numerals or terminal portions of reference numerals have been repeated among the figures to indicate corresponding or analogous elements, which may optionally have similar characteristics.

Figure 4:
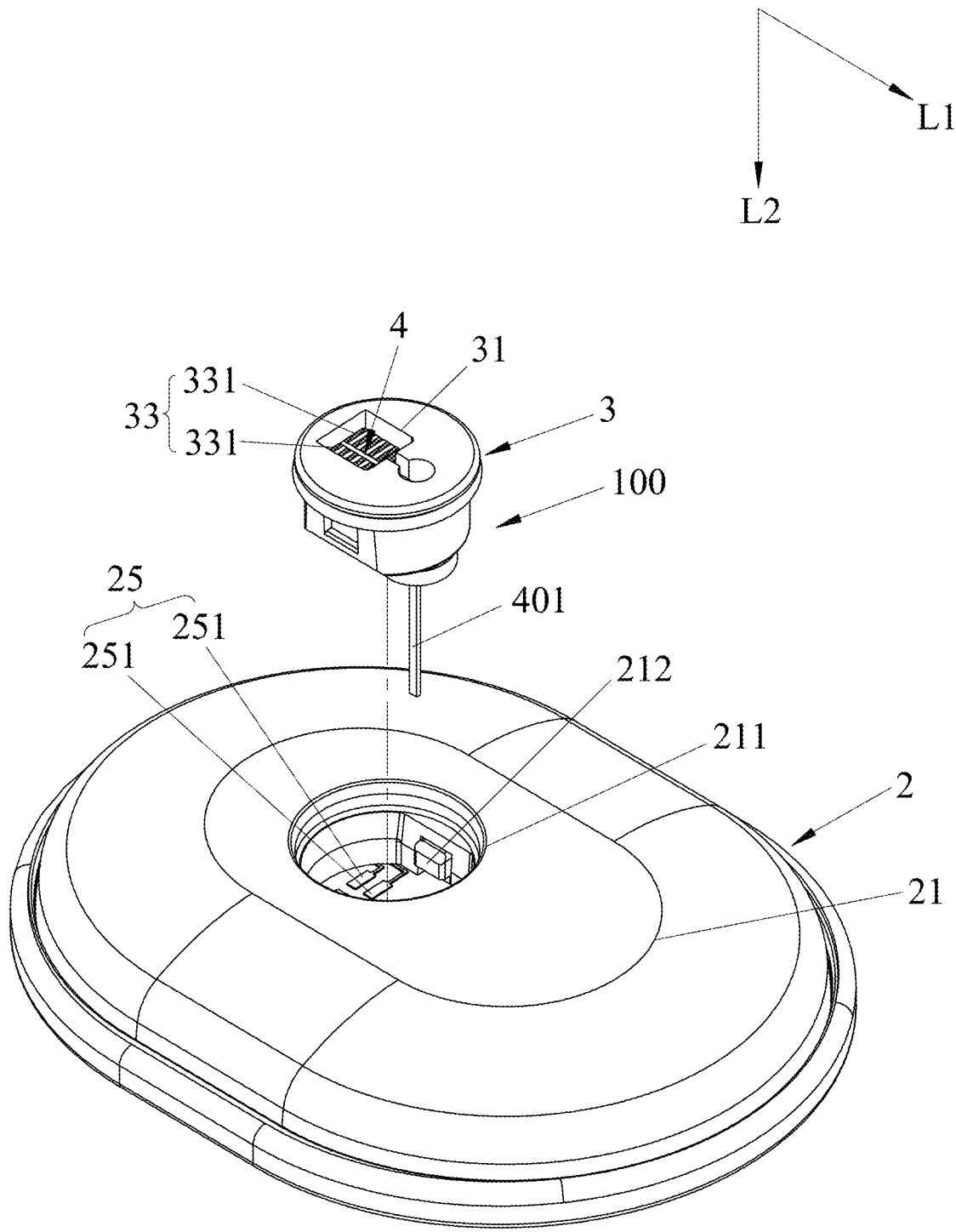
FIG. 4 is a partly exploded perspective view of an embodiment of a biosensing device according to the disclosure.
Figure 7:
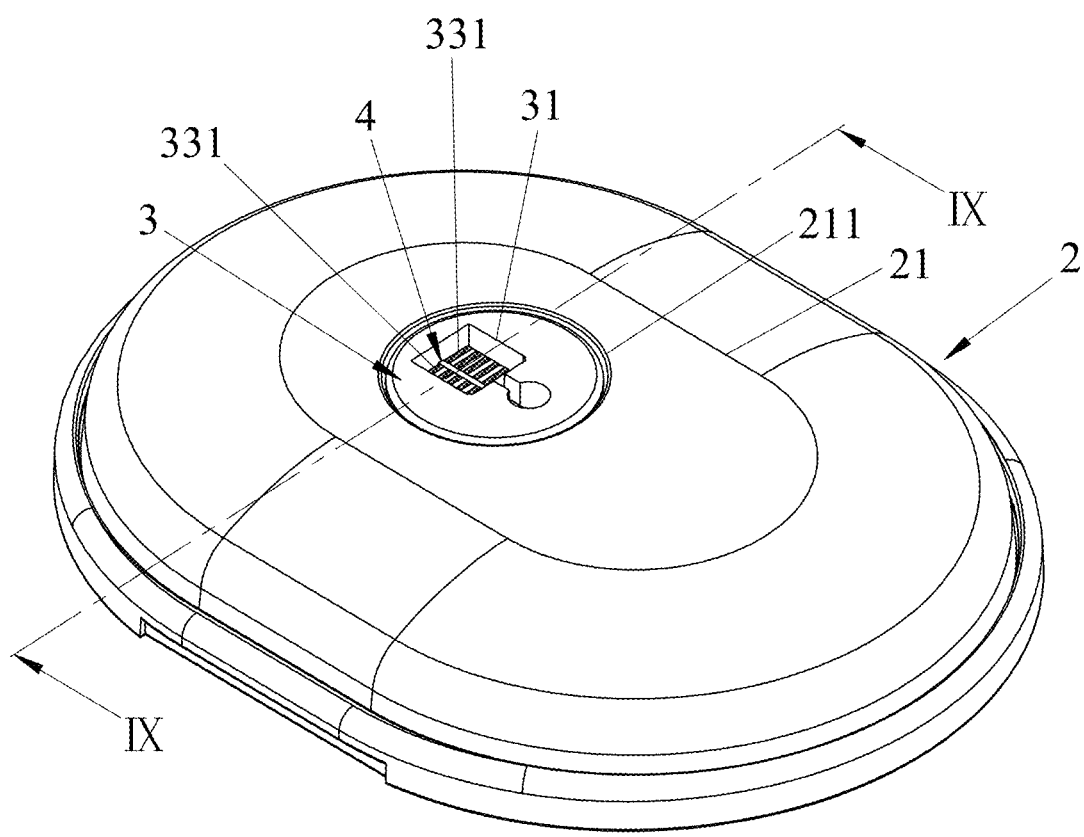
FIG. 7 is an assembled perspective view of the embodiment.
Figure 19:
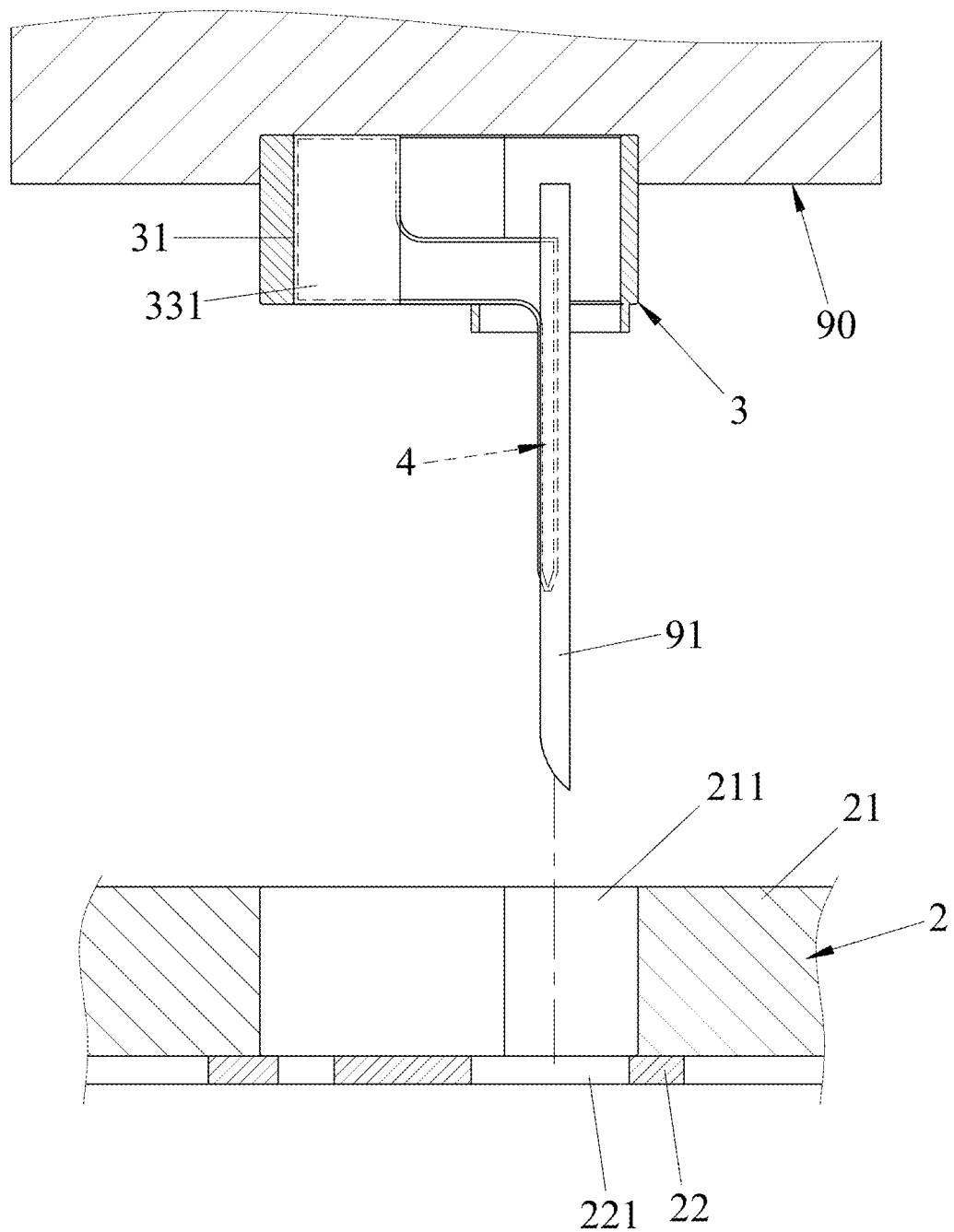
FIG. 19 is a fragmentary sectional view of the embodiment, illustrating the biosensor being installed onto the electric signal transducer via an insertion tool.

Referring to FIGS. 4 and 7, an embodiment of a biosensing device according to the disclosure is adapted to be installed on a host via a guiding needle 91 (see FIG. 19). In the embodiment, the biosensing device is a glucose meter, and includes an electric signal transducer 2 and a sensor module 100. The sensor module 100 includes a fixed seat 3 and a biosensor 4.

Figure 6:
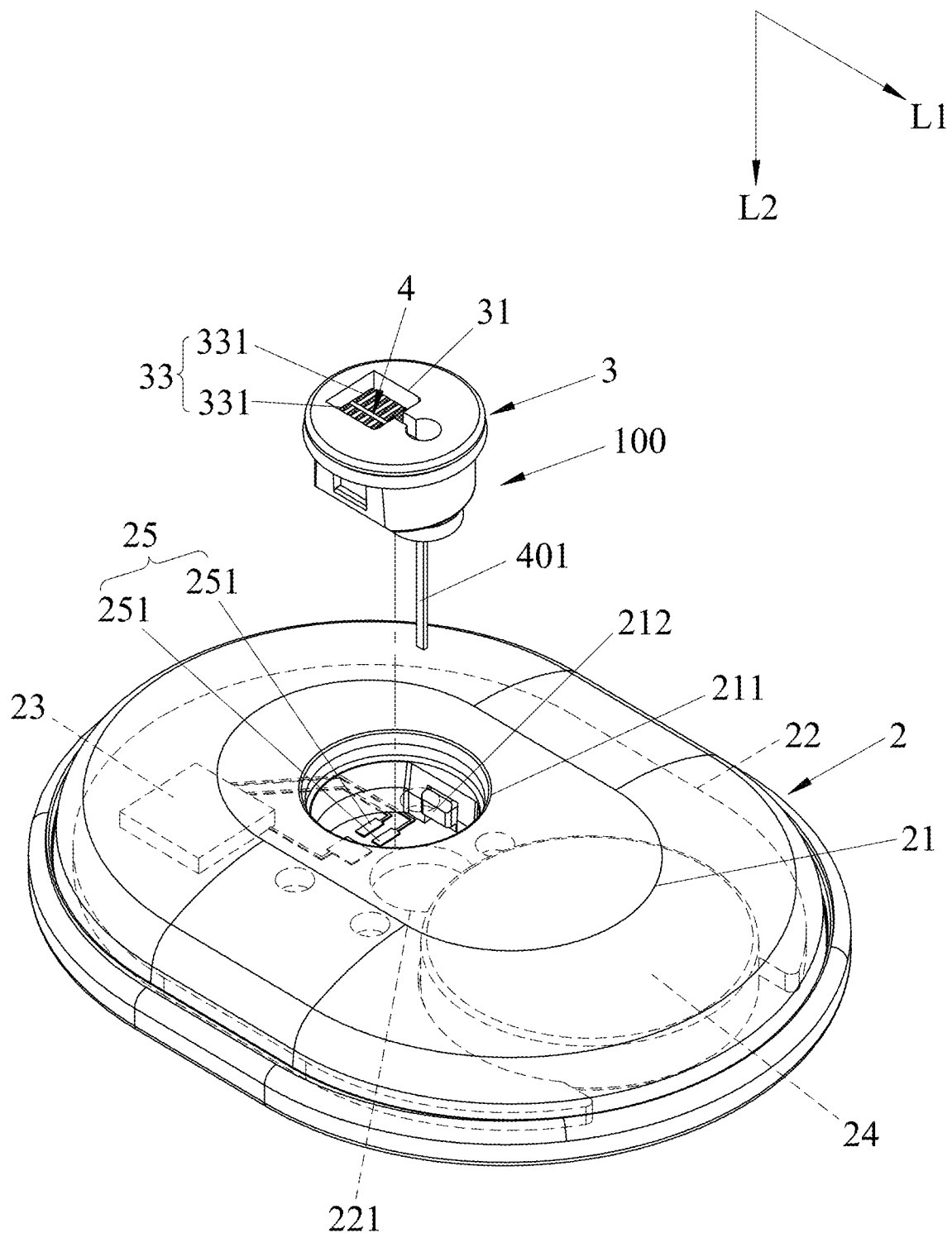
FIG. 6 is a view similar to FIG. 4, illustrating interior components of an electric signal transducer.
Figure 8:
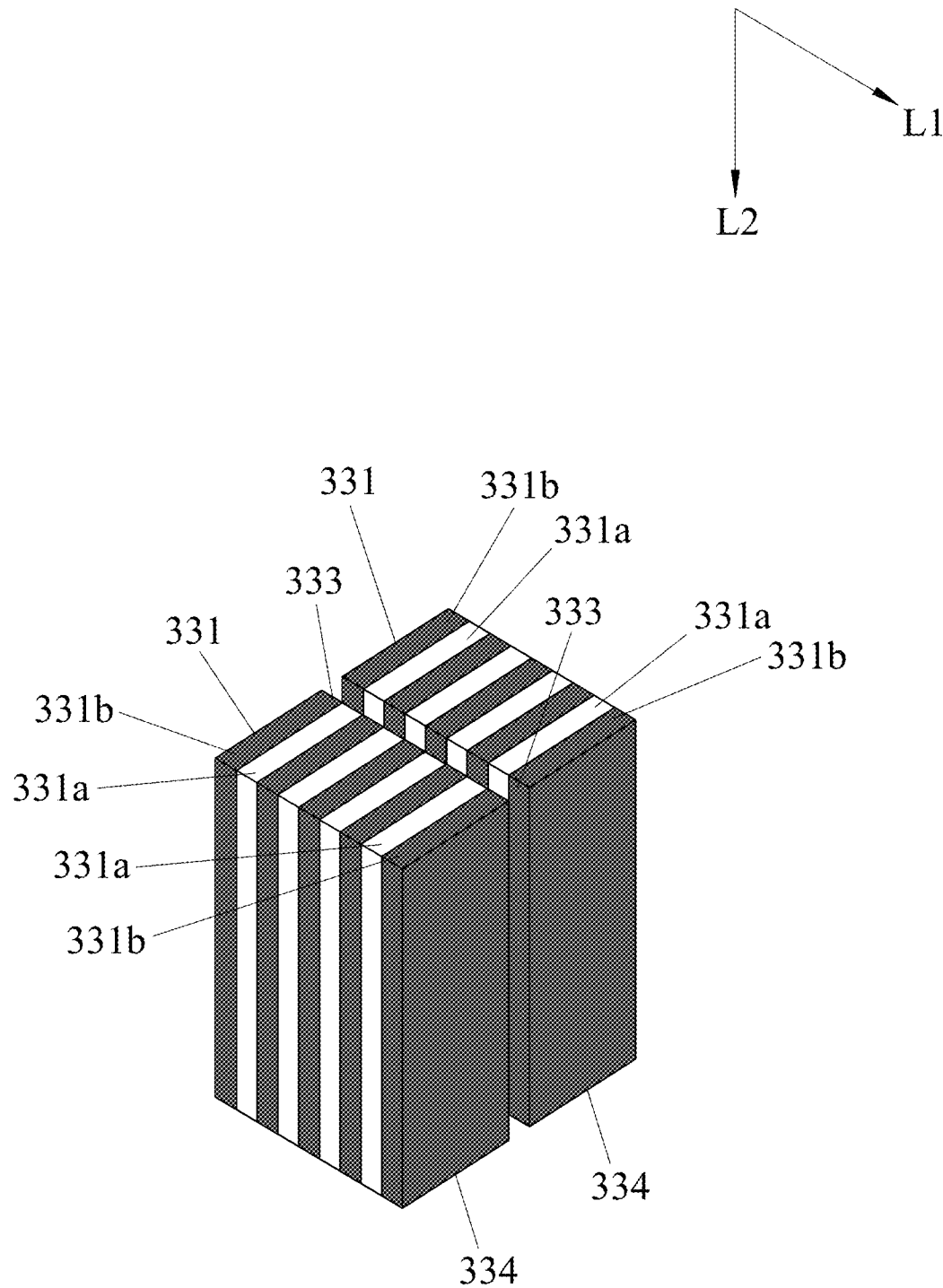
FIG. 8 is a perspective view of two conducting members of the fixed seat the embodiment.
Figure 9:
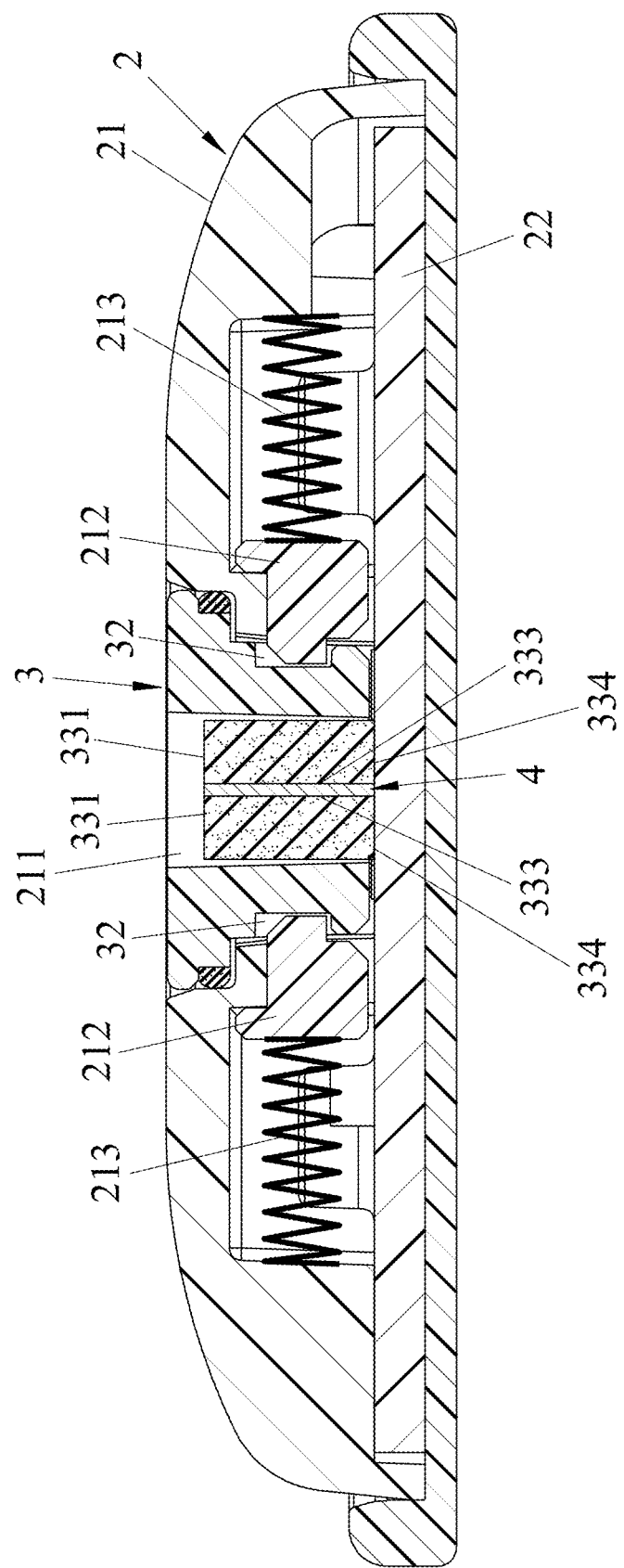
FIG. 9 is a sectional view taken along line IX-IX of FIG. 7.

Referring to FIGS. 6, 8 and 9, the electric signal transducer 2 includes a base 21, a circuit board 22 mounted in the base 21, a transducing unit 23, a battery 24 operable for providing electric power to the transducing unit 23, and an electric signal unit 25. The transducing unit 23, the battery 24, and the electric signal unit 25 are mounted to the circuit board 22.

Figure 11:
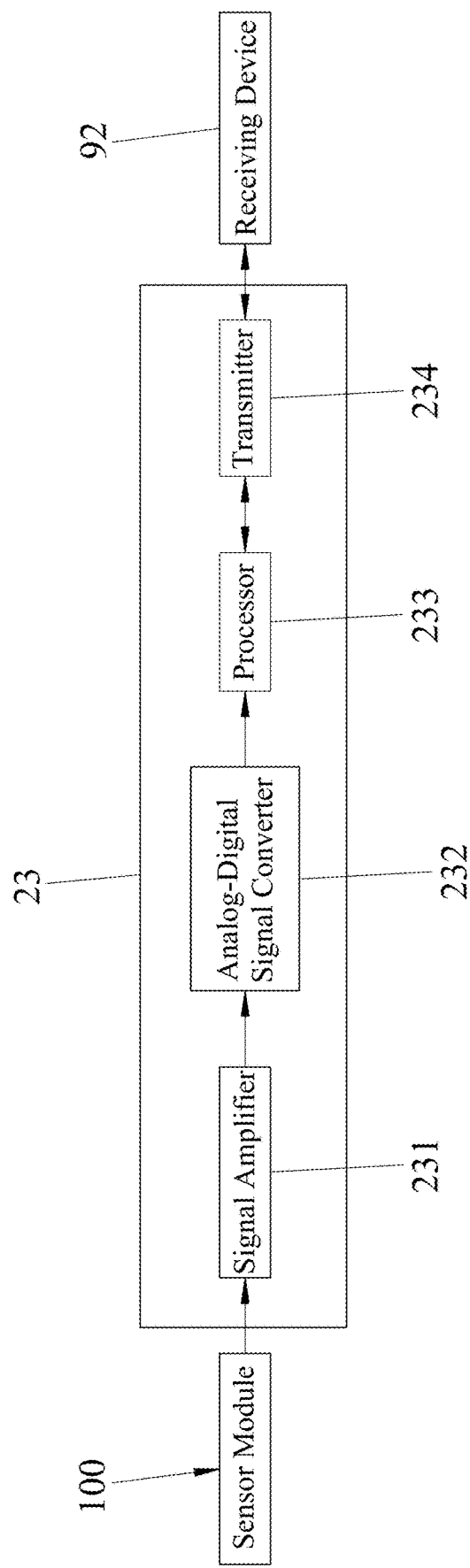
FIG. 11 is a block diagram, illustrating a transducing unit of the electric signal transducer of the embodiment.

The base 21 is adapted to be attached to a skin surface of the host, and has a mounting groove 211, two coupling members 212, and two springs 213. Each of the coupling members 212 is permitted to be resiliently biased by a respective one of the springs 213 to be in a coupling state, where the coupling member 212 partly protrudes into the mounting groove 211. The circuit board 22 has a through hole 221 that corresponds in position to the mounting groove 211. Referring to FIGS. 6 and 11, the transducing unit 23 has a signal amplifier 231, an analog-digital signal converter 232, a processor 233, and a transmitter 234. As the transducing unit 23 is well known in the art and may be internally rearranged to fit different needs, details thereof are omitted for the sake of brevity. The electric signal unit 25 has two spaced-apart electrical contacts 251 that are mounted to the circuit board 22 and that cooperatively define a switch. One of the electrical contacts 251 is electrically connected to the battery 24, and the other one of the electrical contacts 251 is maintained at a ground state. As such, the electrical contacts 251 are not conductive with each other by default, so that the switch is in an open circuit state by default, and that the battery 24 is in the open circuit state as well. In other words, the battery 24 is capable of providing power supply only when the electrical contacts 251 are conductive with each other, and is powered off otherwise.

Figure 5:
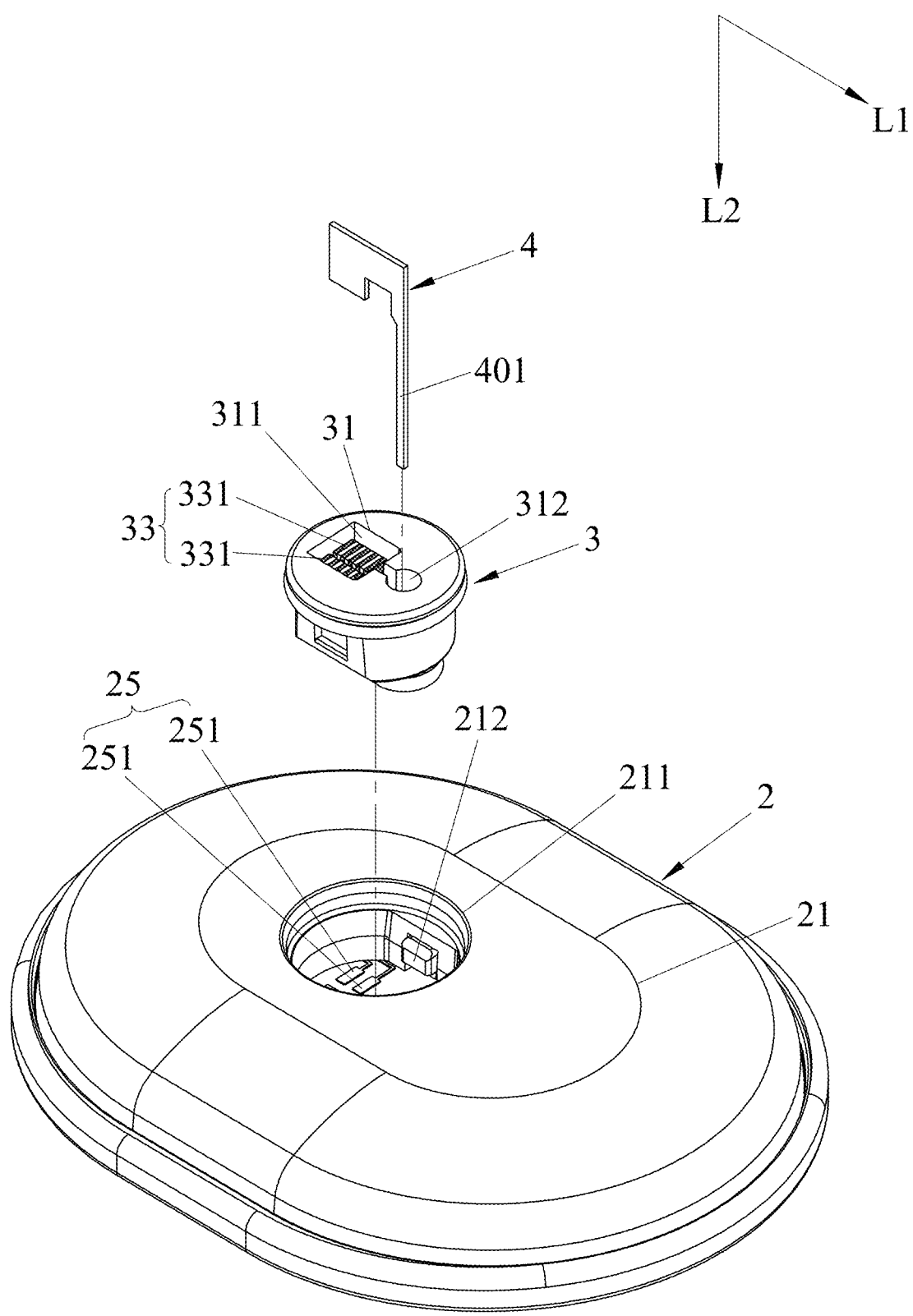
FIG. 5 is a view similar to FIG. 4, illustrating a biosensor of a sensor module being dismounted from a fixed seat of the sensor module.

Referring to FIGS. 4, 6, and 9, the fixed seat 3 of the sensor module 100 is permitted to be removably mounted to the base 21 of the electric signal transducer 2 along a direction of a second axis (L2), and is coupled to the mounting groove 211 thereof. The fixed seat 3 includes a positioning groove 31, two indented grooves 32 that respectively correspond in position to the coupling members 212, and an electric connection unit 33. Referring to FIG. 5, the positioning groove 31 has a connection groove portion 311 for mounting the electric connection unit 33 thereon, and a sensor groove portion 312 for mounting a portion of the biosensor 4 thereon. The sensor groove portion 312 corresponds in position the through hole 221 of the circuit board 22. When the biosensor 4 is mounted to the sensor groove portion 312 of the fixed seat 3, the biosensor 4 is in direct contact with the electric connection unit 33.

The electric connection unit 33 is permitted to be removably and electrically coupled to the circuit board 22 alongside the fixed seat 3, and has two spaced-apart conducting members 331 that are permitted to be electrically connected to the electrical contacts 251 of the electric signal unit 25. Each of the conducting members 331 includes a plurality of conductive layers 331b and a plurality of insulating layers 331a that are disposed in an alternating arrangement (see FIG. 8) along a direction of a first axis (L1), which is not parallel to the second axis (L2). In the embodiment, the conductive layers 331b are synthetic rubbers made of materials such as conductive carbon black and silver powders. Each of the conducting members 331 is a hexahedral structure, and has two non-conducting surfaces that are spaced apart along the first axis (L1) and that are insulated from each other, and four conducting surfaces, one of which is a first conducting surface 333 that is permitted to be electrically connected to the biosensor 4 and another one of which is a second conducting surface 334 that is permitted to be electrically connected to the circuit board 22. In other words, the first and second conducting surfaces 333, 334 are adjacent to each other. In a preferred embodiment, an angle between the first and second conducting surfaces 333, 334 is substantially a right angle. As the conducting surfaces of each of the conducting members 331 are perpendicular to the conductive layers 331b, the conducting surfaces of each of the conducting members 331 are electrically connected to each other via the conductive layers 331b. Due to the relative position of the first and second conducting surfaces 333, 334, when the biosensor 4 is mounted to the sensor groove portion 312 and when the electric connection unit 33 is electrically connected to the circuit board 22, the biosensor 4 is indirectly and electrically connected to the circuit board 22 via the conducting members 331 while it is orthogonally mounted to the circuit board 22. Due to the abovementioned configuration, the biosensor 4 does not need to be bent (or physically reconfigured) to establish electric connection or to transmit signals. As a result, the electric connection and the signals tend to be more stable.

Referring specifically to FIG. 9, when the fixed seat 3 is coupled to the base 21 of the electric signal transducer 2, the coupling members 212 are initially pushed by a bottom portion of the fixed seat 3 to move away from the mounting groove 211 to be in a retracted state, in which the springs are respectively compressed by the coupling members 212 to generate a resilient force. Once the fixed seat 3 is thoroughly disposed in the mounting groove 211 to be in contact with the circuit board 22 in such a way that the coupling members 212 are respectively aligned to the indented grooves 32 of the fixed seat 3, the springs 213 release the resilient force to respectively push the coupling members 212 to be respectively coupled to the indented grooves 32, effectively returning the coupling members 212 back to the coupling state and maintaining close contact between the fixed seat 3 and the circuit board 22.

When the biosensor 4 is mounted to the sensor groove portion 312 of the fixed seat 3, it is electrically connected to the electric signal transducer 2, and is positioned by the conducting members 331. The biosensor 4 is adapted to be guided by a guiding needle 91 for insertion into the host for measuring a biosignal of the host, and correspondingly sending the biosignal to the electric signal transducer 2 in a form of an electric signal. Referring to FIGS. 13 to 18, the biosensor 4 is a substantially flat structure, and a dot-dashed broken line (L) divides the biosensor 4 into a sensing section 401, which is disposed below the broken line (L) and extends along the direction of the second axis (L2), and a signal output section 402, which is disposed above the broken line (L) and extends along the direction of the first axis (L1). The sensing section 401 is permitted to extend through the through hole 221 of the circuit board 22, and at least a portion of the sensing section 401 is permitted to be inserted into the host for measuring the biosignal. The signal output section 402 corresponds in position, is disposed between, and is electrically connected to the conducting members 331 of the electric connection unit 33, and at least a portion of the signal output section 402 is to be electrically connected to the electric signal transducer 2. The first and second axes (L1, L2) are coplanar and cooperatively define an angle (θ) therebetween on the biosensor 4. In the embodiment, the angle (θ) is 90 degrees, but may be anywhere between 4 and 176 degrees, and preferably anywhere from 45 to 135 degrees. The biosensor 4 is unusable if the angle (θ) is not within the abovementioned range.

Figure 12:
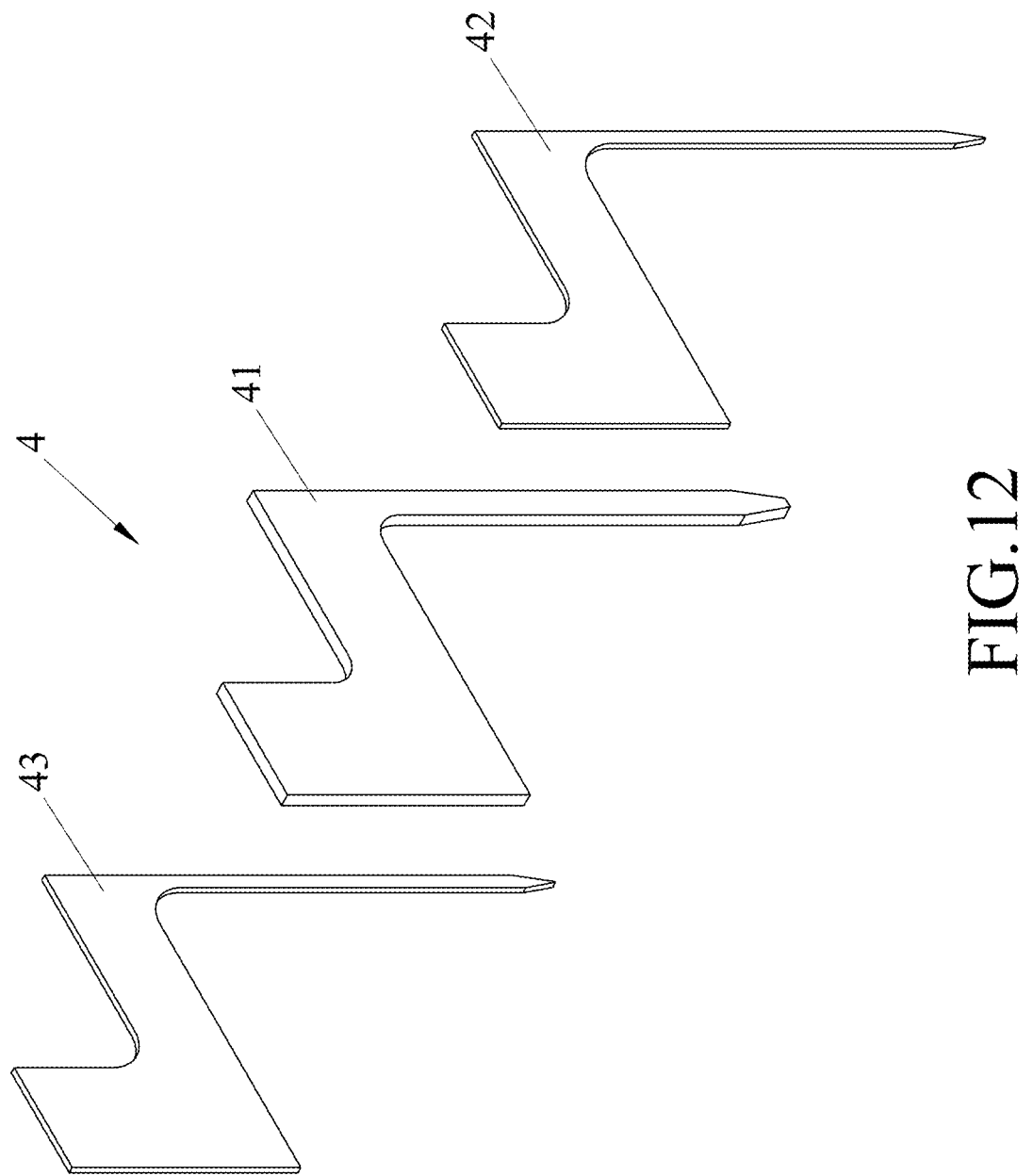
FIG. 12 is an exploded perspective view of the biosensor of the embodiment.
Figure 13:
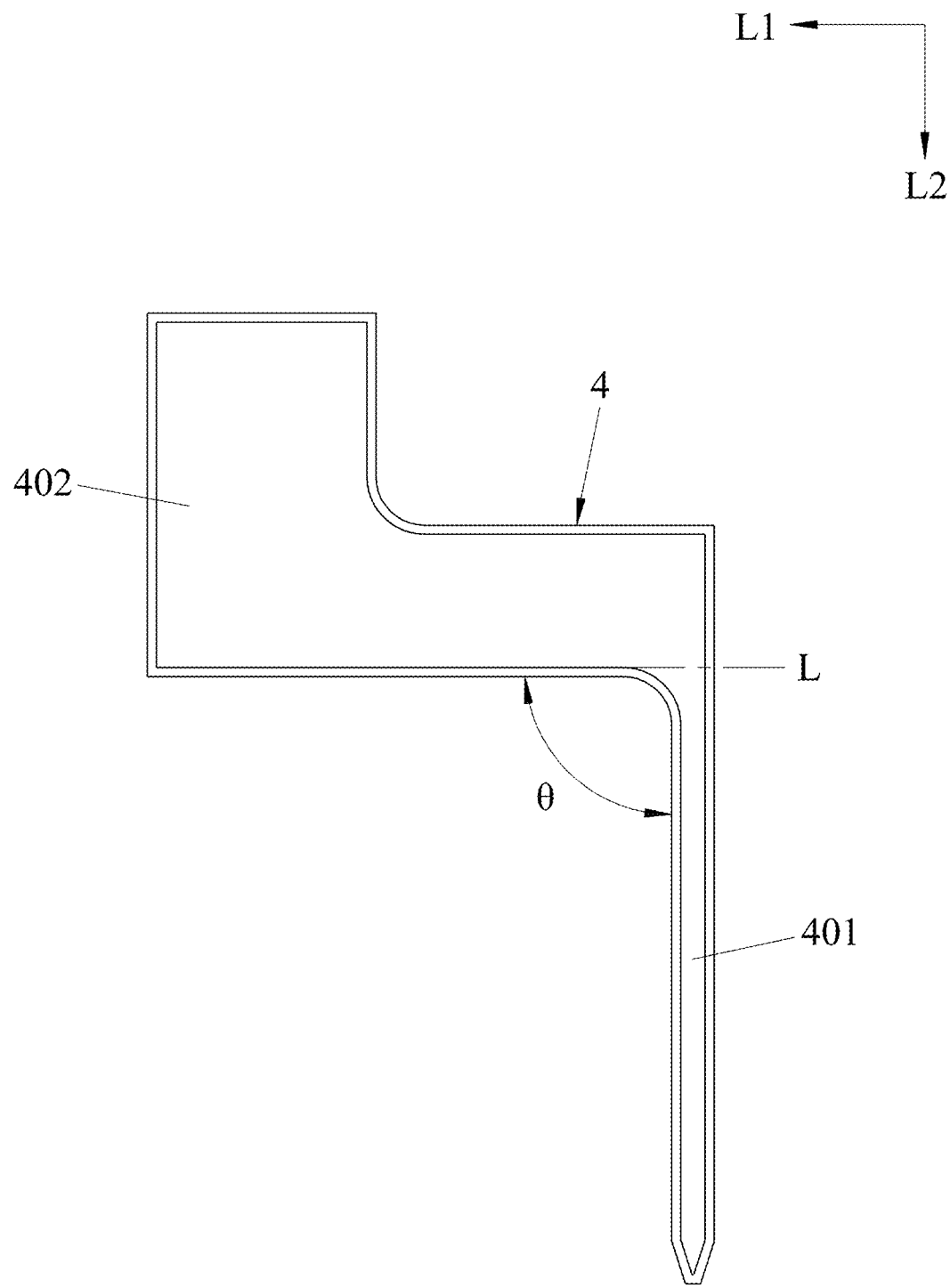
FIGS. 13 to 18 are front views of various modifications of the biosensor of the embodiment.

Referring to FIGS. 12 and 13, the biosensor 4 measures the biosignal via electrodes thereon and an analyte sensing layer. In the embodiment, the biosensor 4 has a base plate 41 that has a thickness ranging from 0.05 millimeters to 0.5 millimeters, a working electrode 42 and a counter electrode 43. The working and counter electrodes 42, 43 are respectively mounted to different sides of the base plate 41, and each of the working and counter electrodes 42, 43 partially defines the sensing section 401, and partially defines the signal output section 402. As the abovementioned sections are interconnected by the electrodes, the biosignal measured by the sensing section 401 is directly transmitted to the signal output section 402 to be sent to the electric signal transducer 2 in the form of the electric signal. The working and counter electrodes 42 may be made of a material selected from platinum, gold, chromium, titanium, tungsten, rhodium, iridium, palladium and graphite, or an alloy thereof. In this embodiment, the counter electrode 43 maybe made of a material selected from platinum, gold, chromium, titanium, tungsten, rhodium, iridium, palladium, silver and silver/silver chloride, or an alloy thereof. Preferably, the counter electrode 43 is made of silver/silver chloride.

Figure 14:
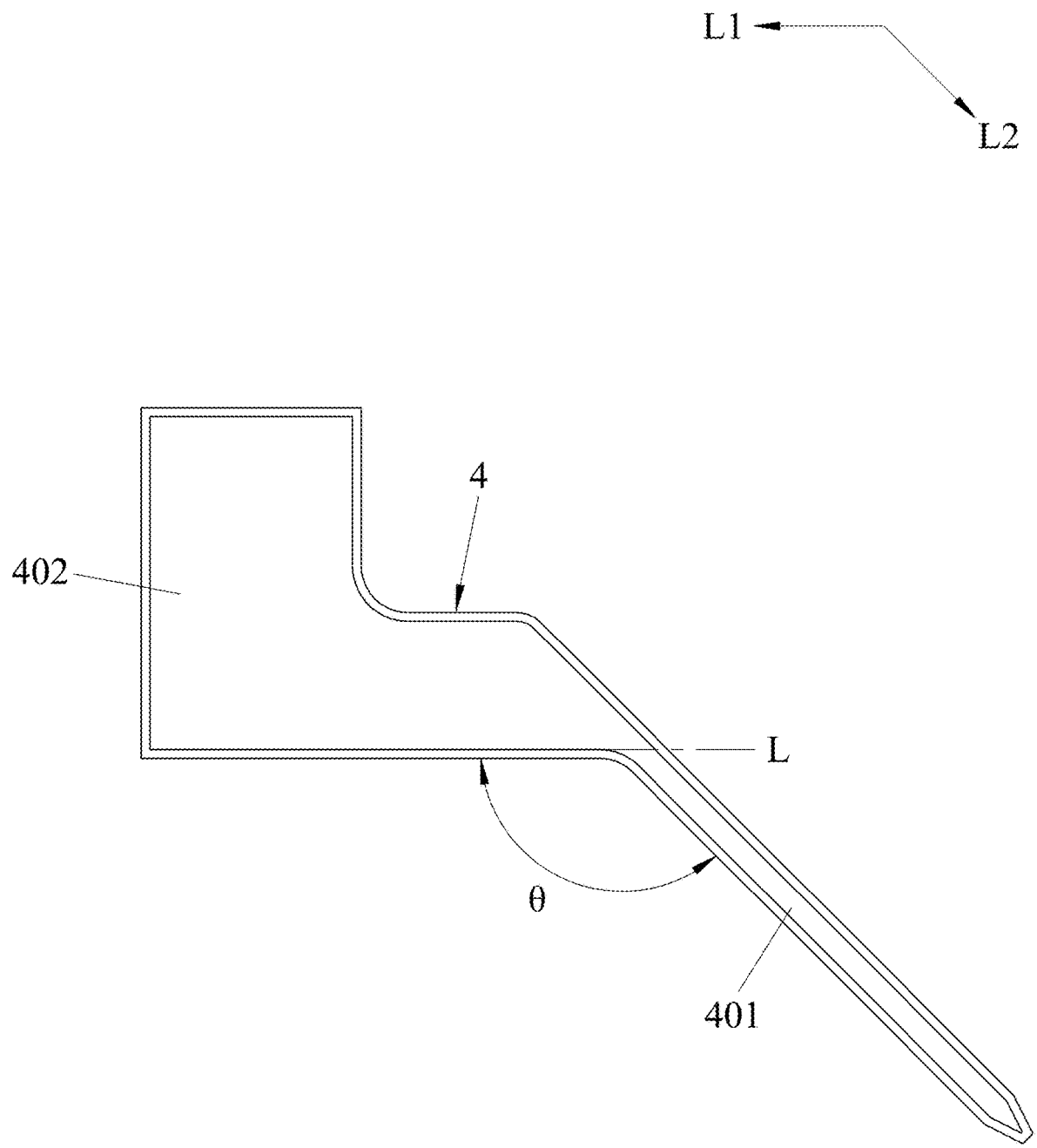
Figure 15:
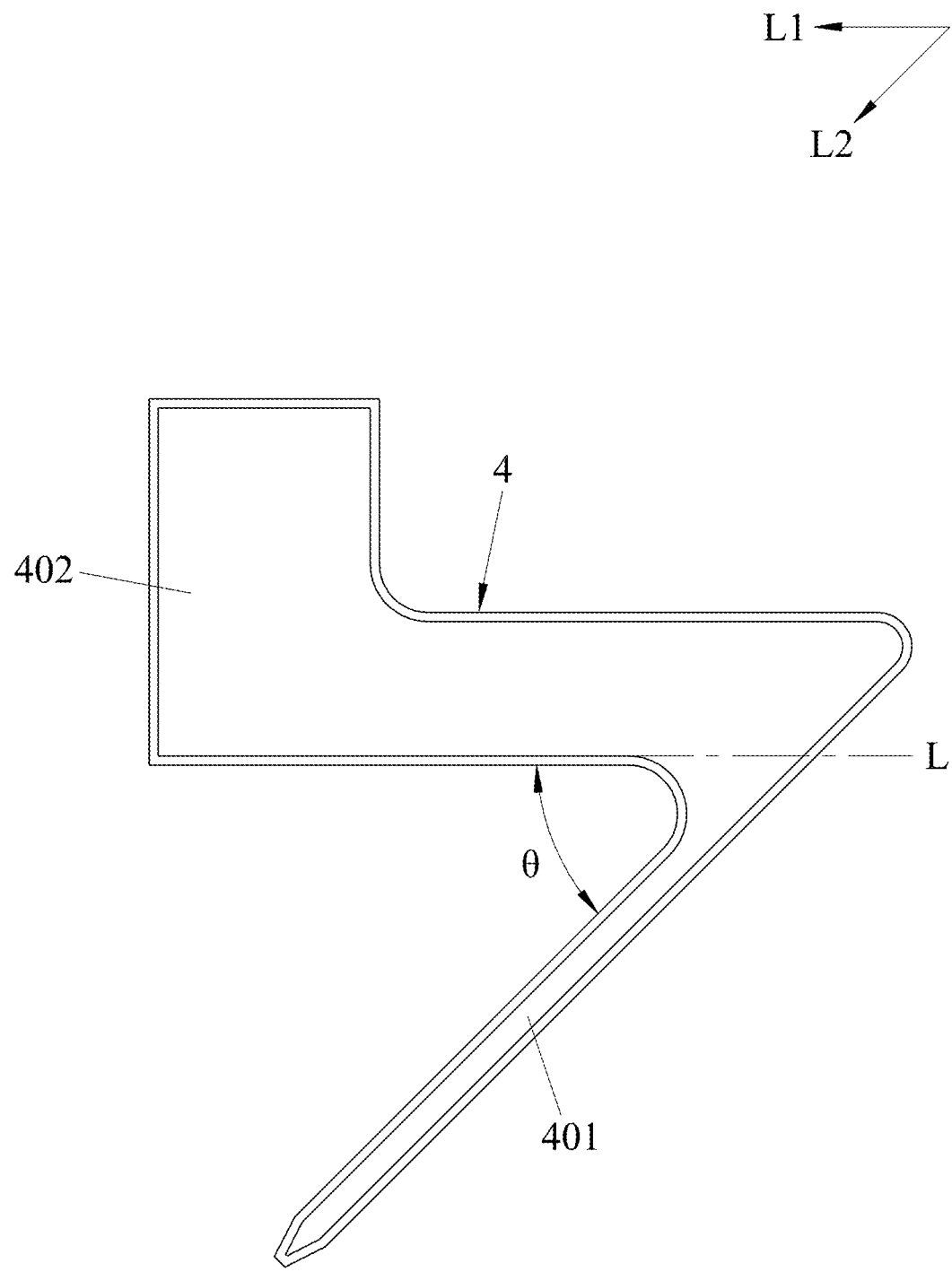
Figure 16:
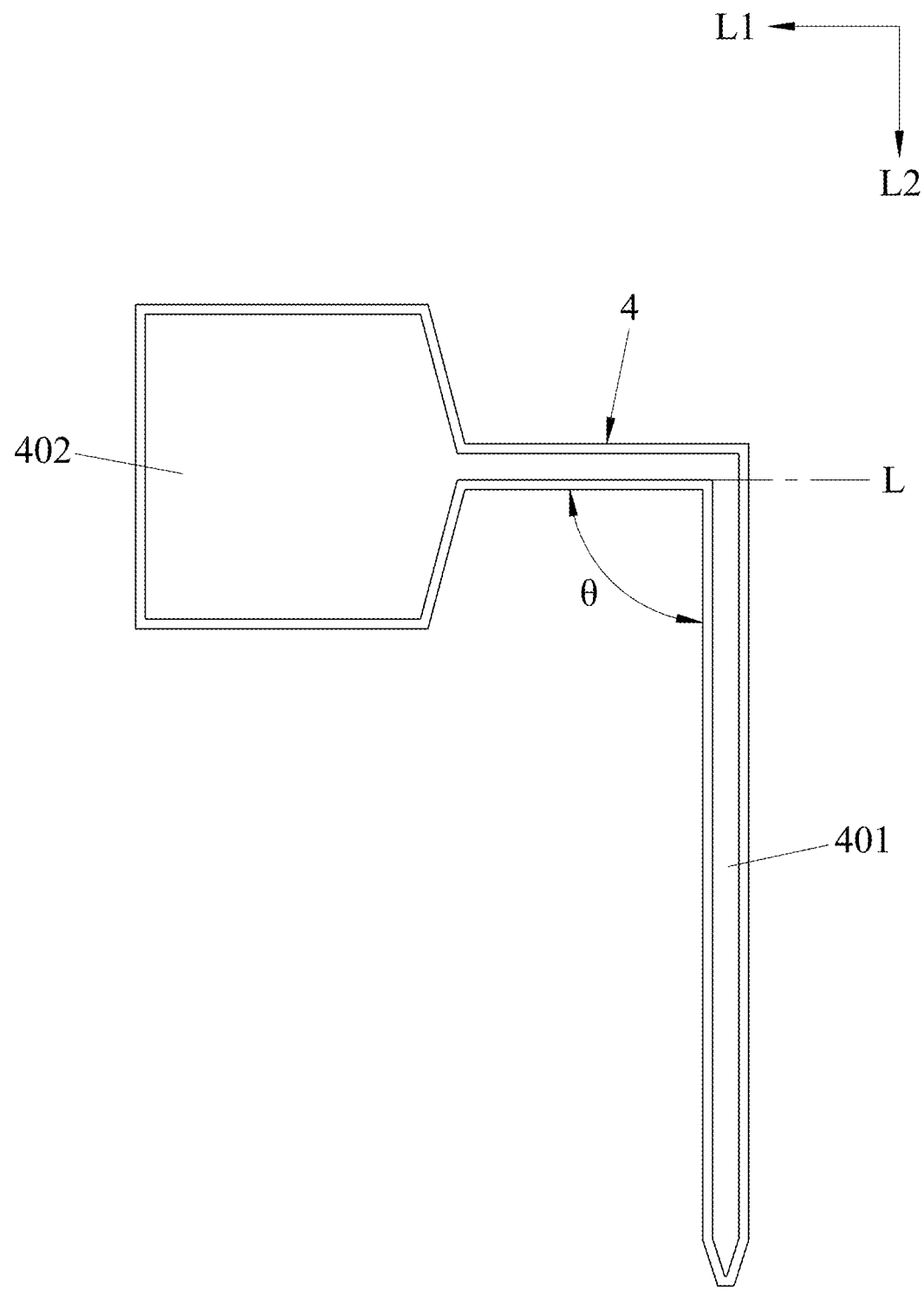
Figure 17:
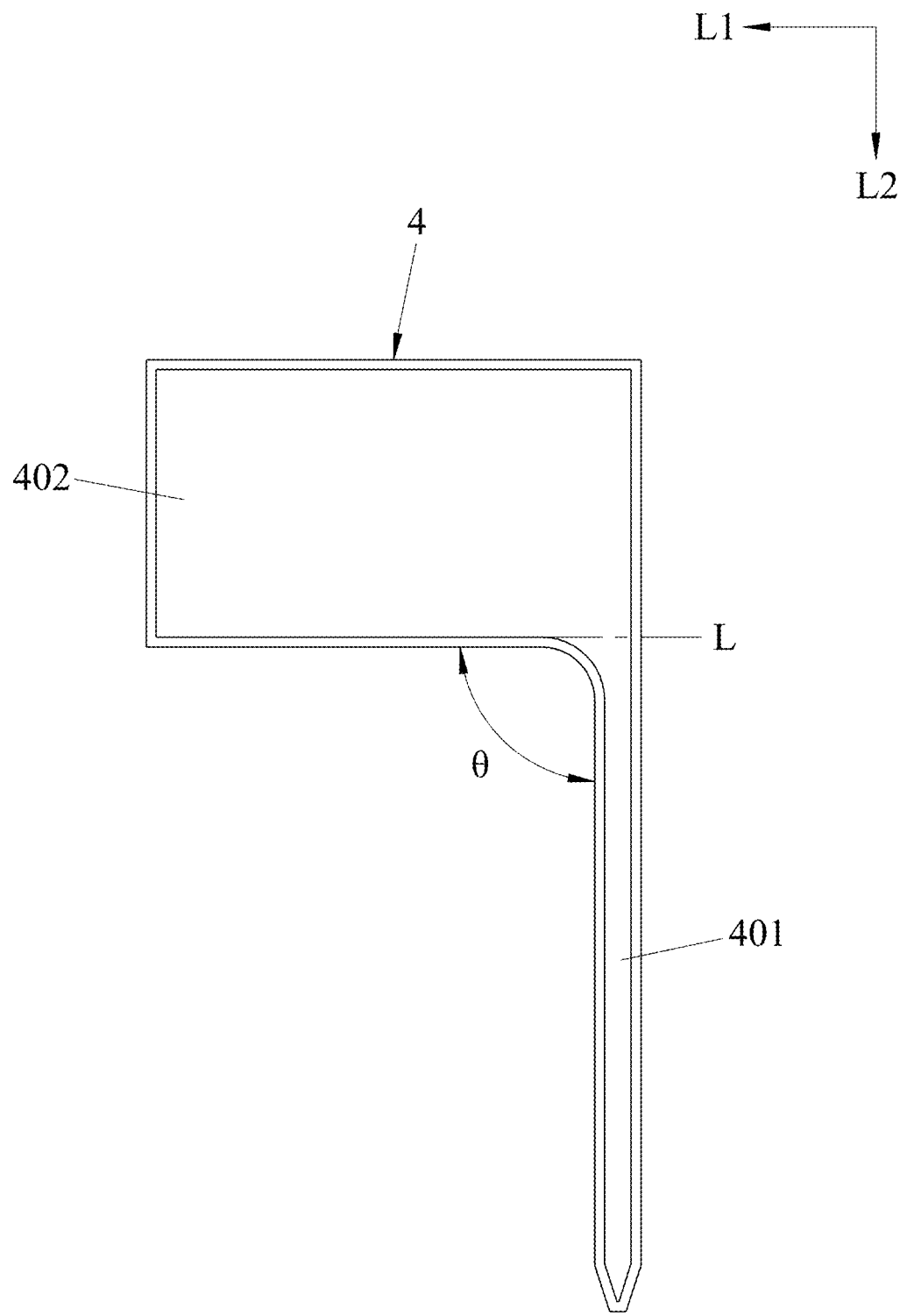

Referring to FIGS. 14 and 15, to optimally insert the biosensor 4 into the host, the angle (θ) on the biosensor 4 preferably can be adjusted accordingly to be anywhere from 4 degrees to 135 degrees. In addition, the signal output section 402 has a surface area larger than that of the sensing section 401, the signal output section 402 can be of any flat shape as long as it is stably and electrically connected to the conducting members 331 (e.g., L-shape, polygon or rectangle). In the embodiment, a length of the sensing section 401 in the direction along the second axis (L2) ranges from 3 millimeters to 20 millimeters (preferably from 5 millimeters to 7 millimeters), and a width thereof ranges from 0.3 millimeters to 1.0 millimeters (preferably from 0.3 millimeters to 0.6 millimeters).

Figure 18:
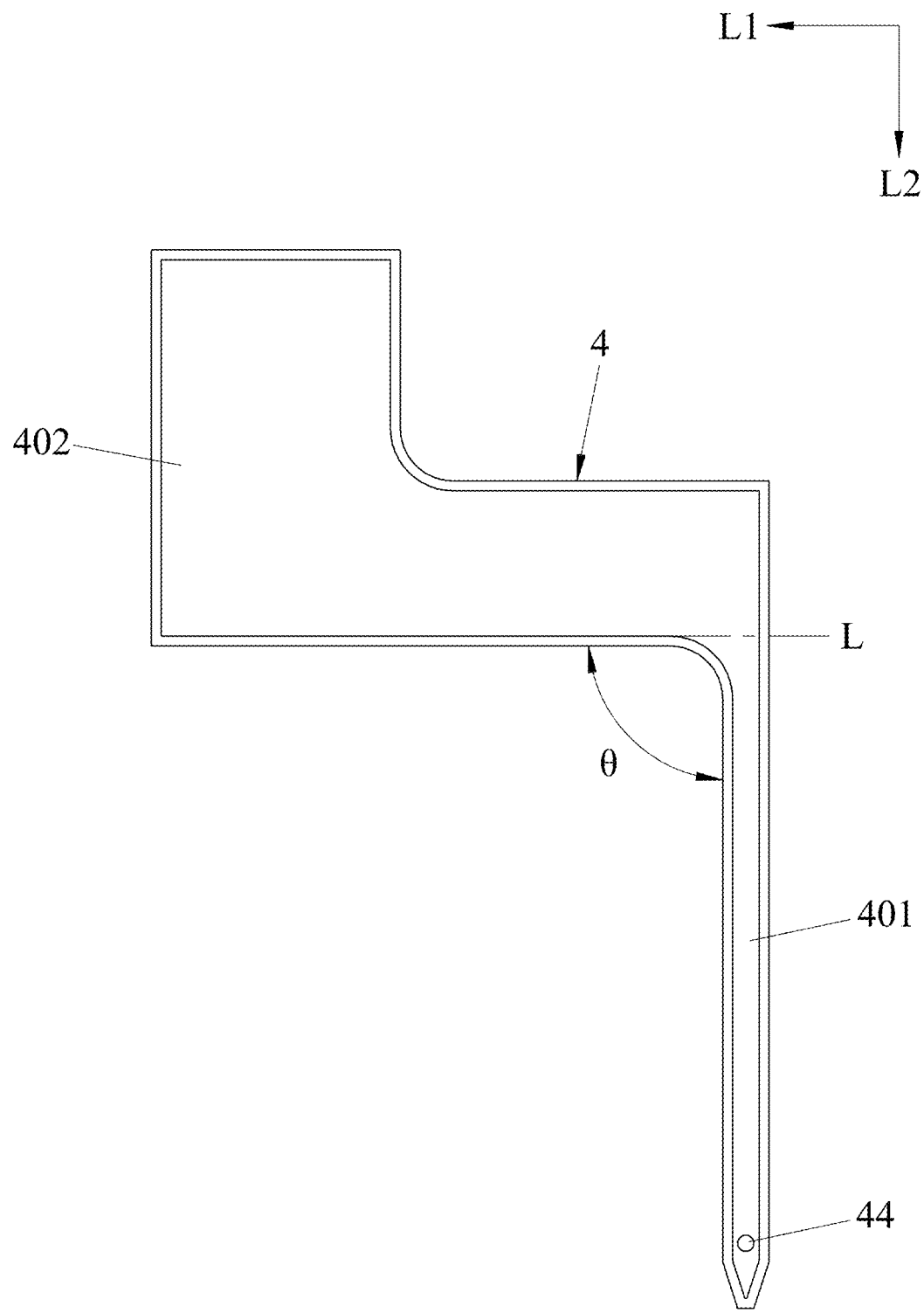

Referring to FIG. 18, in a modification of the embodiment, the biosensor 4 further has a through hole 44 disposed on the sensing section 401. The through hole 44 extends through the base plate 41 and the working and counter electrodes 42, 43 so that blood of the host may flow therethrough easily, thereby improving conductivity and reducing electrical resistance of the biosensor 4. In addition, implementation of the through hole 44 increases the surface area of the analyte sensing layer, improving its stability.

In another modification of the embodiment, the biosensor 4 further has an insulating layer (not shown) that covers the working and counter electrodes 42, 43, and a reference electrode that is mounted on the insulating layer, such that the biosensor 4 has three different electrodes for improving accuracy of the measurement. In other embodiments, the biosensor 4 may have different arrangements of the electrodes, and may have more than three different electrodes for biosignal measurement.

In one of the production methods of the embodiment, a base plate is applied with a conductive coating required on one side for forming the working electrode 42, and with a silver/silver chloride coating on the other side for forming the counter electrode 43. Then, depending on desired physical structure of the biosensor 4, both the conducting coating and the silver/silver chloride coating are laser-cut to form respectively the working and counter electrodes 42, 43. Afterward, the base plate is cut accordingly to form semi-finished product of the biosensor 4. By doing the cutting process in the abovementioned order, cutting blades would not cut into the working and counter electrodes 42, 43, thereby preventing deformation. Lastly, the working electrode 42 is covered with the analyte sensing layer for finishing the biosensor 4. The production method of the biosensor 4 may be different in other embodiments, and is not restricted to the one disclosed herein.

The analyte sensing layer is formed by mixing glucose oxidase, which is reactive with glucose for forming hydrogen peroxide, and water-soluble cross-linker, which keeps the glucose oxidase intact on the biosensor 4 while permitting smaller molecules to pass therethrough. When the working electrode 42 detects presence of hydrogen peroxide, it generates electric signal that indicates glucose levels in blood. The water-soluble cross-linker may be made of disuccinimidyl suberate or glutaraldehyde.

It should be noted that the analyte sensing layer is permitted to be coated with an analyte adjusting layer, which is a porous layer capable of controlling amount of incoming small molecules (e.g. glucose) to thereby adjust amount of small molecules reacting with the analyte sensing layer. The analyte adjusting layer is made from a glucose-permeable polymer, such as Nafion, polyurethane, or polycarbonate. Of the abovementioned glucose-permeable polymers, Nafion is particularly useful for repelling substances with negative charge (e.g. medicines with negative charge) from passing therethrough since it contains groups with negative charge.

Referring to FIGS. 5, 7 and 19, to insert the biosensor 4, the base 21 of the electric signal transducer 2 is attached to the skin surface of the host via adhesives, and the biosensor 4 and the conducting members 331 are to be mounted to the fixed seat 3 to form the sensor module 100. While being mounted, the conducting members 331 are respectively disposed on two opposite sides of the biosensor 4, and are respectively and electrically connected to the working electrode 42 and the counter electrode 43 of the biosensor 4. Then, the sensor module 100 is coupled to the guiding needle 91 of the insertion tool 90. After aligning the guiding needle 91 and the fixed seat 3 to the mounting groove 211 of the base 21, the insertion tool 90 is activated to couple the sensor module 100 to the mounting groove 211, while the biosensor 4 is guided by the insertion needle 91 to be inserted into the host. Afterward, the guiding needle 91 is retrieved by the insertion tool 90 so that at least a portion of the sensing section 401 of the biosensor 4 is disposed in the skin surface of the host, thereby completing the installation process.

In addition, the insertion of the biosensor 4 may be done manually without using an insertion tool. After the electric signal transducer 2 is attached to the skin surface, biosensor 4 of the assembled sensor module 100 is directly coupled to the guiding needle 91. Once the guiding needle 91 is aligned to the through hole 221 of the circuit board 22, the guiding needle 91 is directly and manually inserted into the host by force, thereby guiding the sensing portion 401 of the biosensor 4 into the host, while simultaneously coupling the fixed seat 3 to the mounting groove 211. The guiding needle 91 is retrieved manually afterward.

Because the angle (θ) on the biosensor 4 is premade, the angle (θ) does not change substantially before and after the insertion operation of the biosensor 4. As such, the biosensor 4 would not be bent after being inserted into the host, thereby maintaining the quality of the electric connection between the biosensor 4 and the electric signal transducer 2.

When the biosensor 4 and the electric connection unit 33 is mounted to a main body of the fixed seat 3, the signal output section 402 of the biosensor 4 is positionally clamped by the conducting members 331, which are urged by groove walls of the positioning groove 31 to tightly contact the biosensor 4. The conducting members 331 are relatively malleable for maintaining the biosensor 4 therebetween, and are spaced apart from each other in a distance slightly smaller than the thickness of the biosensor 4. In addition, referring specifically to FIG. 10, as bottom ends of the conducting members 331 are slightly protruded relative to bottom ends of the signal output section 402 of the biosensor 4 and the fixed seat 3, when the fixed seat 3 is thoroughly coupled to the electric signal transducer 2, the conducting members 331 tightly contact the electrical contacts 251 of the electric signal unit 25, thereby ensuring stable electric connection thereamong.

Figure 10:
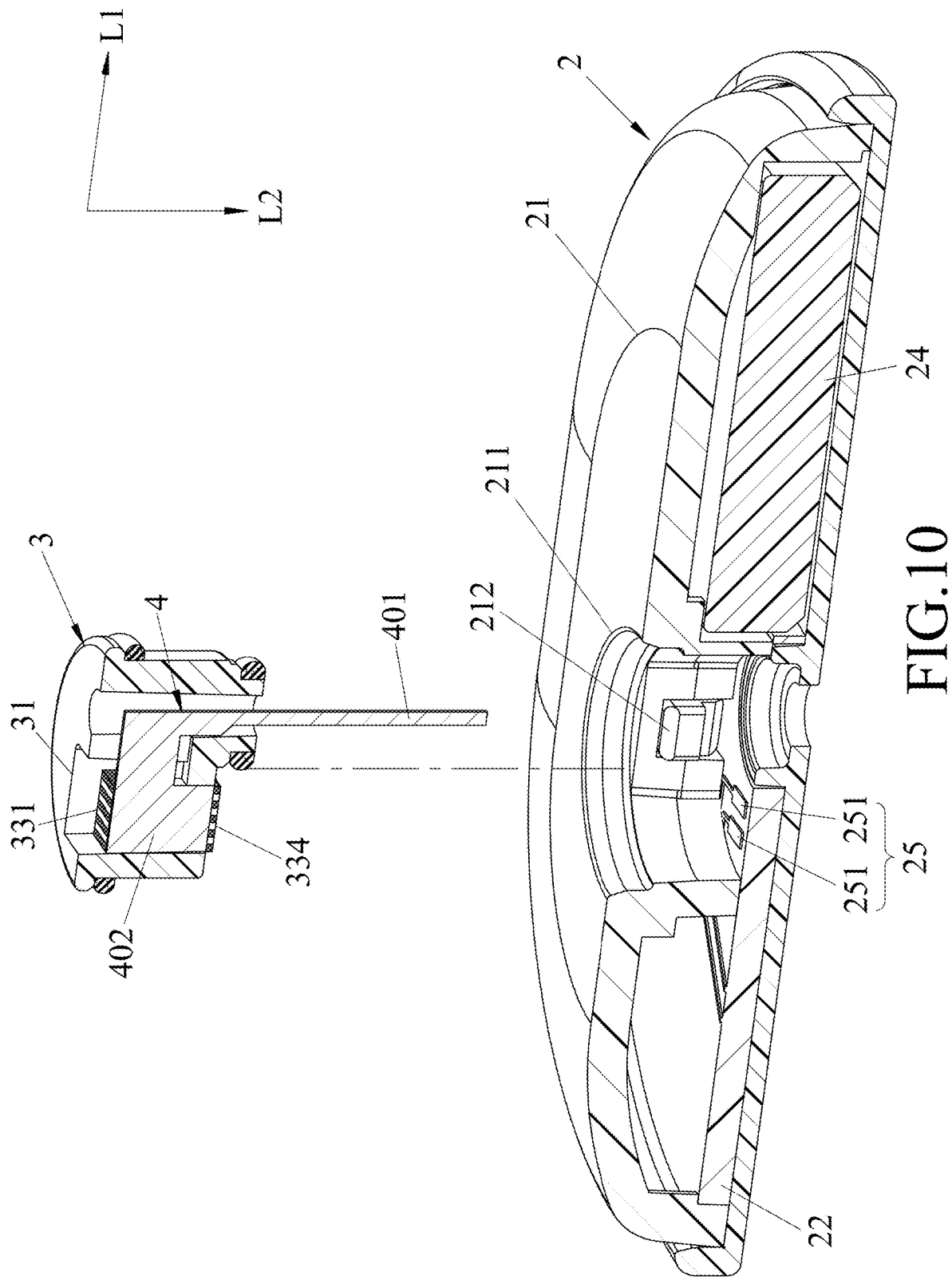
FIG. 10 is a cutaway perspective view of the embodiment, illustrating the sensor module being uncoupled from the electric signal transducer.
Figure 20:
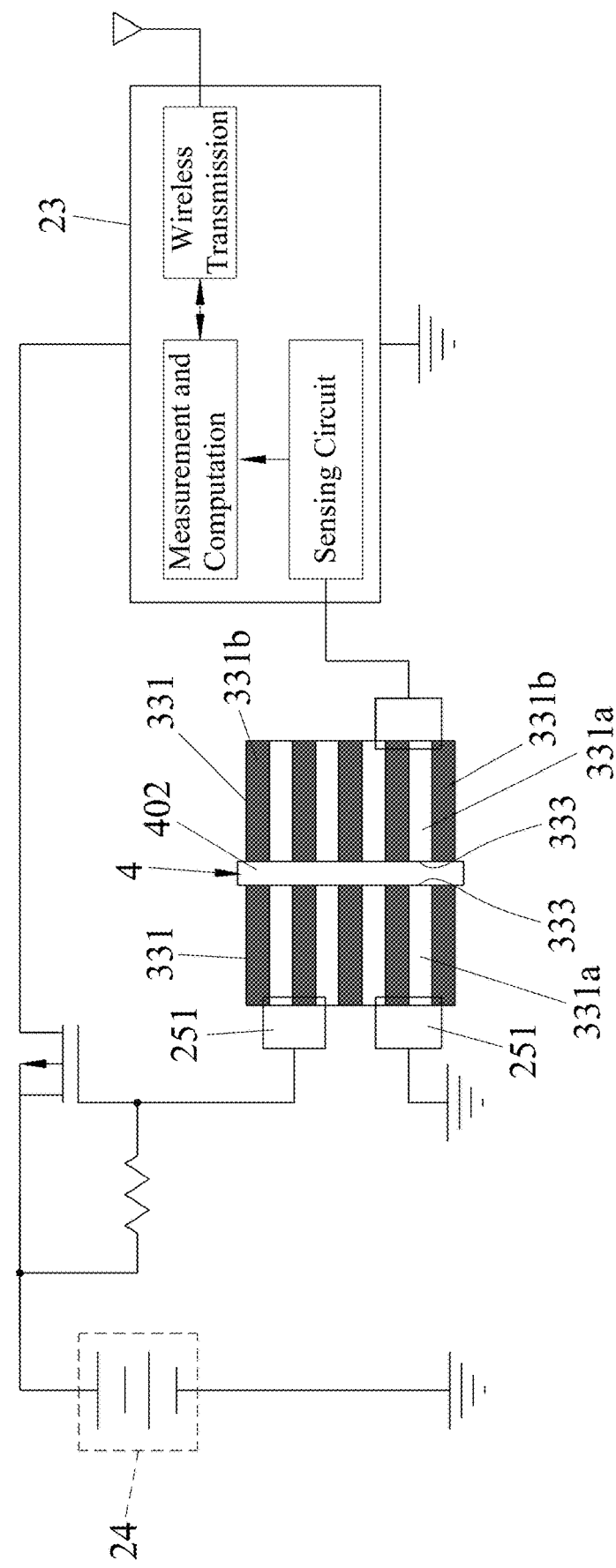
FIG. 20 is a circuit diagram of the embodiment.

Referring to FIG. 20 in conjunction with FIGS. 8 to 10, each of the electrical contacts 251 of the electric signal unit 25 of the electric signal transducer 2 is electrically connected to at least one of the conductive layers 331b of the conducting members 331 to be further in electric connection with the biosensor 4. It should be noted that because the conducting members 331 includes a plurality of insulating layers 331a and a plurality of conductive layers 331b disposed in an alternating arrangement, any two of the conductive layers 331b are not directly conductive with each other. When the assembled sensor module 100 is coupled to and electrically connected to the electrical contacts 251 of the electric signal unit 25, the electrical contacts 251 become a complete circuit via the signal output section 402 of the biosensor 4, such that the battery 24 provides power supply to the biosensor 4 via the conducting members 331 of the electric connection unit 33. In a preferred embodiment, when the electrical contacts 251 become a complete circuit, in addition to providing electric power to the sensor module 100 for measuring the biosignal, the battery 24 also simultaneously provides electric power to the transducing unit 23, such that the transducing unit 23 is permitted to receive the biosignal measured by the biosensor 4 of the sensor module 100, and is adapted to send the biosignal to a receiving device 92 (see FIG. 11).

Figure 21:
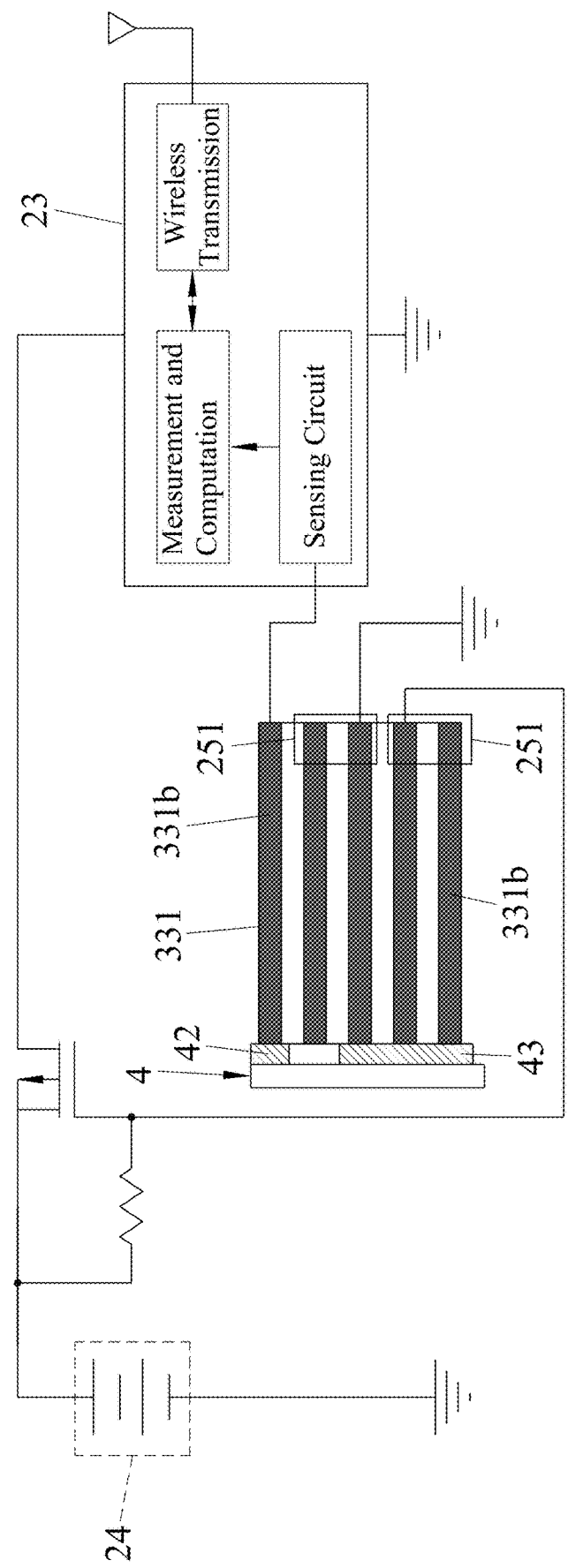
FIG. 21 is a diagram similar to FIG. 20, illustrating the embodiment having only one conducting member, and electrical contacts thereof being electrically connected to different conductive layers of the conducting member.
Figure 22:
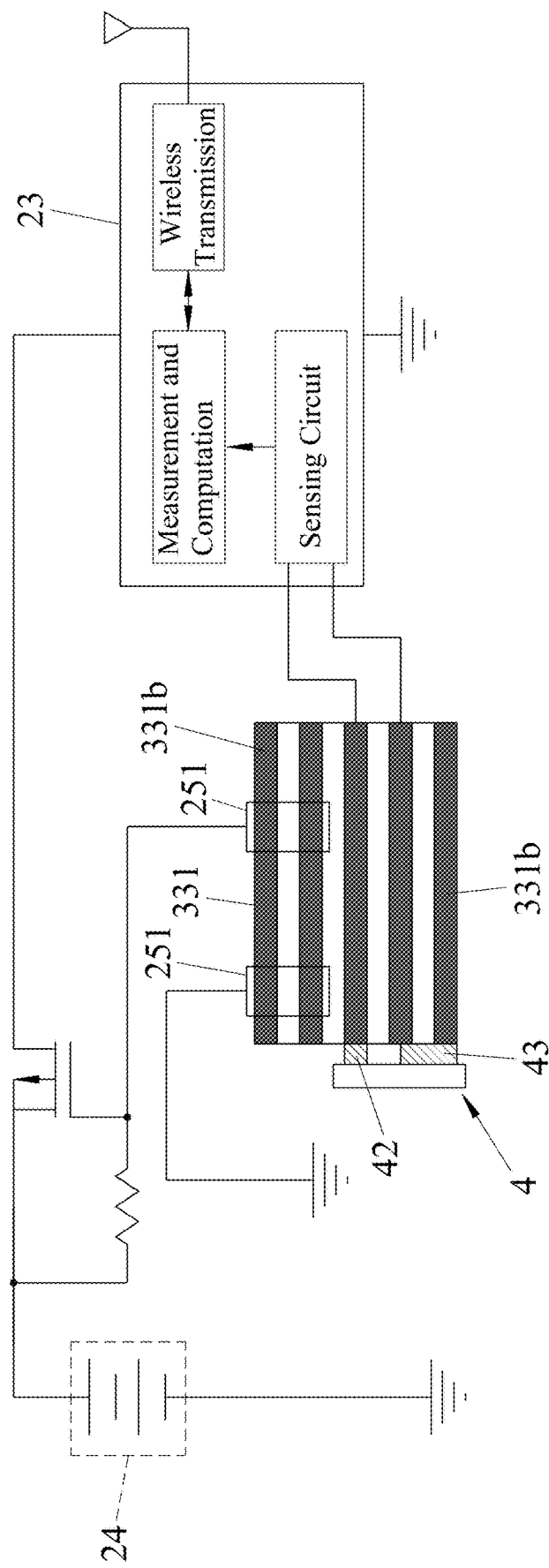
FIG. 22 is a diagram similar to FIG. 21, illustrating the electrical contacts of the embodiment being electrically connected to same conductive layer of the conducting member.

In a modification of the embodiment, the number of the conducting members 331 is one, in which one side of the biosensor 4 is in direct contact with the conducting member 331, while the opposite side of the biosensor 4 is urged by the groove wall of the positioning grooves 31 of the fixed seat 3. Referring to FIGS. 21 and 22, the working and counter electrodes 42, 43 are spaced apart from each other, and are mounted to the same side of the base plate 41. The electrical contacts 251 of the electric signal unit 25 may either be connected to different conductive layers 331b of the conductive member 331 (see FIG. 21) or the same conductive layers 331b of the conductive member 331 (see FIG. 22). Whether or not the number of the conducting members 331 is one or two, the electric power of the battery 24 is only consumed when the electric signal transducer 2 is coupled to the sensor module 100.

In this embodiment, each of the electrical contacts 251 of the electric signal unit 25 is connected to two of the conductive layers 331b, but is not restricted as such. In other embodiments, each of the electrical contacts 251 may be connected to one or more than two of the conductive layers 331b.

Figure 23:
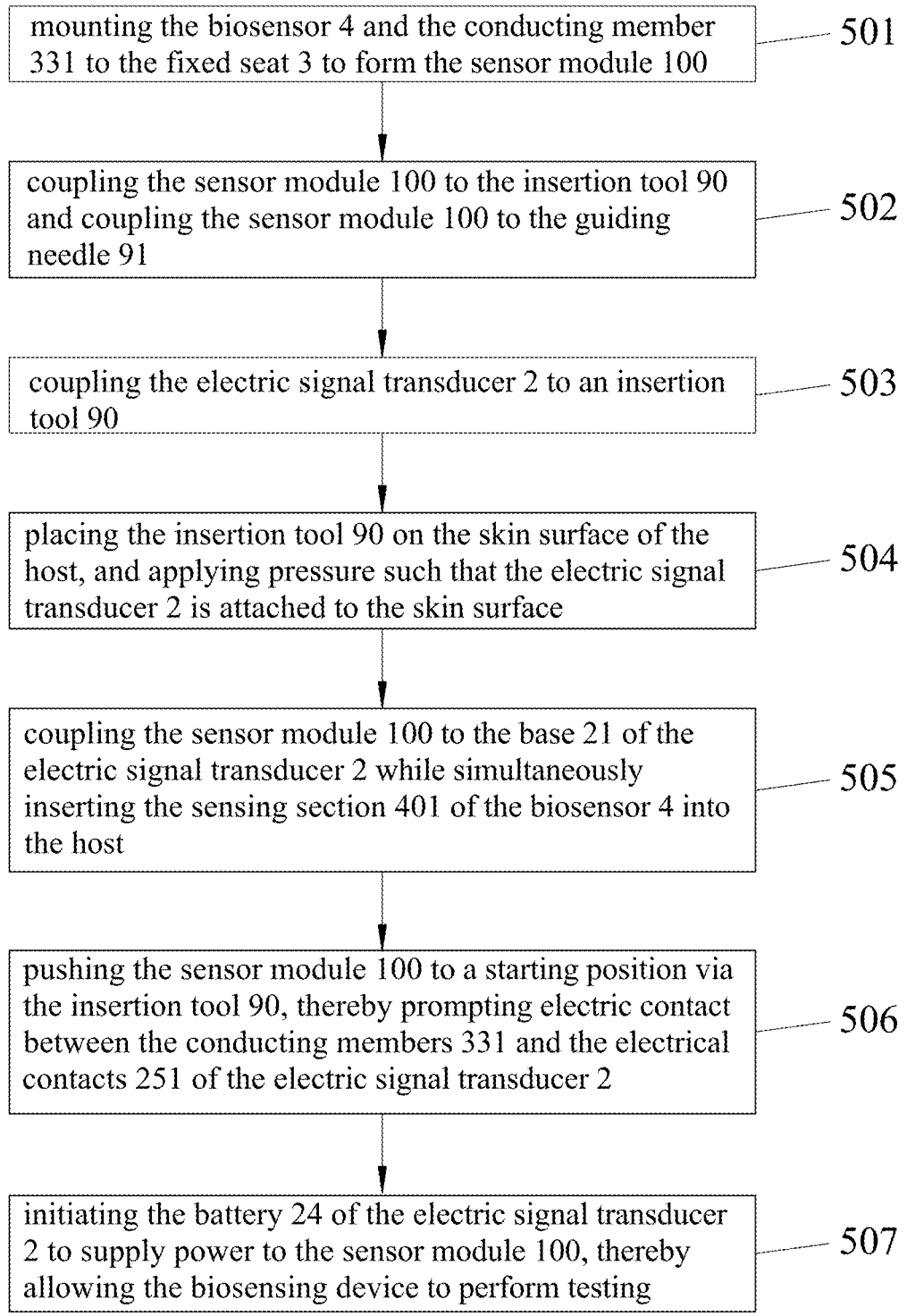
FIG. 23 is an activation flow diagram of the embodiment.

Referring to FIG. 23 in conjunction with FIGS. 6, 9 and 19, the biosensing device activation method includes the following steps:

501) mounting the biosensor 4 and the conducting member 331 to the fixed seat 3 to form the sensor module 100;

502) coupling the sensor module 100 to the insertion tool 90 and coupling the sensor module 100 to the guiding needle 91;

503) coupling the electric signal transducer 2 to an insertion tool 90 along the direction of the second axis (L2);

504) placing the insertion tool 90 on the skin surface of the host, and applying pressure such that the electric signal transducer 2 is attached to the skin surface;

505) coupling the sensor module 100 to the base 21 of the electric signal transducer 2 while simultaneously inserting the sensing section 401 of the biosensor 4 into the host;

506) pushing the sensor module 100 to a starting position via the insertion tool 90, thereby prompting electric contact between the conducting members 331 and the electrical contacts 251 of the electric signal transducer 2; and 507) initiating the battery 24 of the electric signal transducer 2 to supply power to the sensor module 100, thereby allowing the biosensing device to perform testing.

In step 501, the biosensor 4 is clamped by the malleable conducting members 331 which are urged by groove walls of the positioning groove 31 to tightly contact the biosensor 4, so the biosensor 4 is steadily positioned within the positioning groove 31 without additional adhesives.

Overall, since the biosensor 4 does not have to be bent for measuring the biosignal after being inserted into the host, the biosensor 4 is less likely to be damaged throughout the process. In addition, as the sensor module 100 and the electric signal transducer 2 may be separated before their uses, the battery 24 of the electric signal is powered off completely as the electrical contacts 251 of the electrical signal transducer 2 are in the open circuit state at this time, conserving power consumption before the biosensor 4 draws electric power therefrom.

In the description above, for the purposes of explanation, numerous specific details have been set forth in order to provide a thorough understanding of the embodiment. It will be apparent, however, to one skilled in the art, that one or more other embodiments maybe practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A biosensing device activation method comprising steps of:
   a) mounting a biosensor and a conducting member to a fixed seat to form a sensor module, the conducting member including a plurality of conductive layers and a plurality of insulating layers that are disposed in an alternating arrangement along a direction of a first axis;
   b) coupling the sensor module to an insertion tool, and coupling the sensor module to a guiding needle;
   c) coupling an electric signal transducer to the insertion tool along a direction of a second axis not parallel to the first axis, two electrical contacts of the electric signal transducer being in an open circuit state;
   d) placing the insertion tool on a skin surface of a host, and applying pressure such that the electric signal transducer is attached to the skin surface;
   e) coupling the sensor module to a base of the electric signal transducer while simultaneously inserting a sensing section of the biosensor into the host;
   f) pushing the sensor module to a starting position via the insertion tool, thereby prompting electric contact between the conducting member and the electrical contacts of the electric signal transducer; and
   g) initiating the battery of the electric signal transducer to supply power to the sensor module, thereby allowing the biosensing device to perform testing.

2. The biosensing device activation method as claimed in claim 1, wherein the battery is powered off completely when the electrical contacts of the electric signal transducer are in the open circuit state.

3. The biosensing device activation method as claimed in claim 1, wherein steps f) and g) are simultaneously executed by executing step e).

4. The biosensing device activation method as claimed in claim 1, wherein, in executing step e), the sensor module and the electric signal transducer are moved relative to each other along the direction of the second axis.

* * * * *